United States Patent [19]

Baker et al.

[11] Patent Number: 4,837,399

[45] Date of Patent: Jun. 6, 1989

[54] NAHTHOQUINONE ANTIBIOTICS FROM FUSARIUM SOLANI

[75] Inventors: Robert A. Baker, Lake Wales; James H. Tatum, Winter Haven, both of Fla.

[73] Assignee: The United States of America as represented by the Secretary of Agriculture, Washington, D.C.

[21] Appl. No.: 192,085

[22] Filed: May 10, 1988

[51] Int. Cl.[4] ............................. C12P 1/02; C12P 7/26
[52] U.S. Cl. ............................. 514/468; 514/682; 435/126; 435/156; 435/170; 435/929
[58] Field of Search ................ 514/682, 468; 435/156, 435/170, 929, 126

[56] References Cited

U.S. PATENT DOCUMENTS 3,959,468  5/1976  Burmeister ........................... 424/122
4,238,405  12/1980  Felix ..................................... 548/166

OTHER PUBLICATIONS

H. Kern, "The Naphthazarins of Fusarium", Ann. Phytopathol. 10: 327–345 (1978).
J. H. Tatum et al., "Three Further Naphthoquinones Produced by *Fusarium Solani*", Phytochemistry 24: 3019–3021 (1985).
T. W. Flegel et al., "A New Naphthoquinone Antibiotic From a New Species of Yeast", J. Antibiot. 37: 325–329 (1984); Chem. Abst. 101: 267 (1984).
V. P. Papageorgiou et al., "Study on the Antibiotic Fraction of Alkanna *Tinctoria* Tausch", Chem. Chron. 9: 57–63 (1980); Chem. Abst. 94: 120 (1981).

*Primary Examiner*—Herbert J. Lilling
*Attorney, Agent, or Firm*—M. Howard Silverstein; John D. Fado; Mervin E. Brokke

[57] ABSTRACT

Three naphthoquinones isolated from cultures of *Fusarium solani* were found to be effective antibiotics against gram-positive bacteria. Controlling the dissolved oxygen concentration in the fermentation medium between 0.7 and 2.0 ppm resulted in maximum yields of the naphthoquinones. 2,3-Dihydro-5,8-dihydroxy-6-methoxy-2-hydroxymethyl-3-(2-hydroxypropyl)-1,4-naphtholenedione was the most effective antibiotic.

4 Claims, No Drawings

NAHTHOQUINONE ANTIBIOTICS FROM FUSARIUM SOLANI

BACKGROUND OF THE INVENTION

This invention relates to new naphthoquinone derivatives which exhibit antibiotic activity.

Many antibiotics used in medicine today are secondary metabolites produced by cultures of various species of fungi, or are semi-synthetic analogs derived from these metabolites. The ability of bacteria to develop resistance to antibiotics over a period of time requires that new sources and new compounds be continually discovered as replacements. In some cases bacterial resistance to a given antibiotic can by overcome be effecting a minor change in the molecular structure of the drug. However, the constant selective pressure of antibiotic exposure has led to the emergence of highly resistant strains of certain pathogens, such as *Staphylococcus aureus*. The broad spectrum resistance acquired by these bacterial strains greatly increases the hazard of such infections.

*Fusarium solani* is a soil-borne fungus which, when grown on certain media, elaborates a class of secondary metabolites known as naphthoquinones. Several of these compounds have been shown to have antibiotic activity against certain bacteria and fungi [H. Kern, Ann. Phytopathol. 10(3): 327–345 (1978)].

Studies relating soil aeration to disease state have focused on the effect of low oxygen stress on the plant, or on the plant-pathogen interaction, without considering the effect of such stress on the pathogen itself. *F. solani* responds to low pH and other imposed stresses by synthesizing a number of naphthoquinone derivatives [D. Parisot et al., J. Gen. Microbiol. 126: 443–457 (1981)]. These compounds, and others derived therefrom via oxidation, possess both phytotoxic and antibiotic properties [A. W. McColloch et al., Can. J. Chem. 60: 2943–2949 (1982)].

Minor structural differences profoundly influence the antimicrobial activities of these compounds. Some have little measurable inhibitory activity, while others of very similar structure are quite potent. Presence or lack of antimicrobial activity cannot be deduced simply by examination of the compound's structure.

SUMMARY OF THE INVENTION

We have now discovered three previously unrecognized naphthoquinone derivatives from *Fusarium solani* which are potent antibiotics.

In accordance with this discovery, it is an object of this invention to define previously unknown antibiotic activity for the compound 2,3-dihydro-5,8-dihydroxy-6-methoxy-2-hydroxymethyl-3-(2-hydroxypropyl)-1,4-naphthalene dion It is a further object of this invention to define previously unknown antibiotic activity for the compound 2,3-dihydro-5-hydroxy-4-hydroxymethyl-8-methoxy-2-methyl-naphtho[1,2-b] furan-6,9-dione.

It is a further object of this invention to define previously unknown antibiotic activity for the compound 5,8-dihydroxy-2-methoxy-6-hydroxymethyl-7-(2-hydroxypropyl)-1,4

It is also an object of this invention to define optimal conditions for producing naphthoquinone antibiotics from *Fusarium solani*.

Other objects and advantages of this invention will be readily apparent from the ensuing detailed description.

DETAILED DESCRIPTION OF THE INVENTION

The naphthoquinone antibiotics which are the subject of this invention were isolated by a fermentation procedure from a culture of *Fusarium solani* identified as BP15-8, NRRL No. 15980. This strain is on deposit with the ARS Culture Collection, Peoria, IL 61604 [J. H. Tatum et al., Phytochemistry 24(12): 3019–3021 (1985)].

Structures of the subject naphthoquinones are shown below.

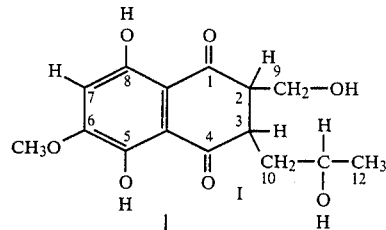

(1) 2,3-dihydro-5,8-dihydroxy-6-methoxy-2-hydroxymethyl-3-(2-hydroxypropyl)-1,4-naphthalenedione

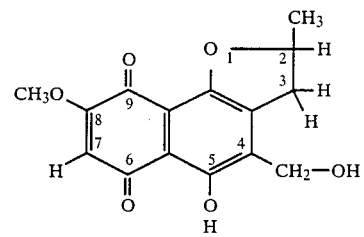

(2) 2,3-dihydro-5-hydroxy-4-hydroxymethyl-8-methoxy-2-methyl-naptho[1,2-b]furan-6,9-dione

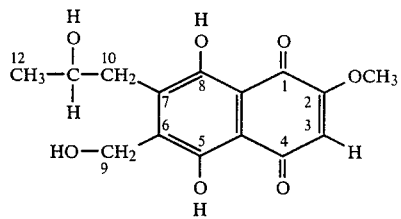

(3) 5,8-dihydroxy-2-methoxy-6-hydroxymethyl-7-(2-hydroxypropyl)-1,4-naphthalenedione These materials may be obtained by isolation from fermentation broths or alternatively by synthetic or semi-synthetic means. Compounds 2 and 3 may be obtained by chemical modification of compound 1.

Under usual cultural conditions, the primary products of *F. solani* cultures are cis- and trans-dihydrofusarubin. An unexpected finding was the lowering the cultures' available dissolved oxygen to a level greater than 0.7 ppm but less than 2 ppm altered the biosynthetic capacity of the organism resulting in the production of 2,3-dihydro-5,8-dihydroxy-6-methoxy-2-hydroxymethyl-3-(2-hydroxypropyl)-1,4-naphthalene ppm dissolved oxygen, the *F. solani* culture elaborated dihydrofusarubins, while at dissolved oxygen levels less than 0.7 ppm, naphthoquinone biosynthesis was eliminated. The preferred level of oxygen was found to be about 1.1 ppm.

Although specific reagents and quantities thereof are given in the culture medium formulation in Example 1, most of these are not critical. Any carbon source promoting adequate mycelial growth would suffice, as would any combination of inorganic components sufficient to sustain growth. However, some form of ammonium salt such as ammonium nitrate must be incorporated in the medium to allow the pH to decline during the fermentation to approximately 2.5. Culture pH must be maintained between 2.0 and 3.0; pH values of 2.0 and below prevent mycelial growth and respiration, while at pH values above 3.0 formation of naphthoquinones is not initiated. Adjustment of pH to 2.5 may also be accomplished with addition of mineral acids such as hydrochloric acid.

Antibiotic activity of these compounds was established in vitro but, as will be apparent to those skilled in the arts pertaining to antibiotic usage, the compounds, besides being used as such, will for utilitarian purposes commonly be formulated in a manner consistent with the desired mode of application. This would include, but not be limited to, solution or suspension in unguents or creams for topical application, formulation with suitable inert diluents and binders for incorporation in tablets or capsules, and solution in appropriate solvents for parenteral usage.

The naphthoquinones encompassed herein are effective in controlling a variety of organisms. Without desiring to be limited thereto, bacteria of particular interest known to be vulnerable to treatment are bacteria pathogenic to mammals, especially grampositive bacteria of the Staphylococcus and Streptococcus genera. These naphthoquinones were found to be inactive against gram-negative bacteria and filamentous fungi.

Purified compounds were tested for antibiotic activity by dissolving in dimethyl sulfoxide and utilizing a standard broth microdilution assay. The smallest amount of compound resulting in complete inhibition of bacterial growth is the minimum inhibitory concentration (MIC).

The organisms used in the tests were three strains of gram-positive bacteria: *Staphylococcus aureus, Streptococcus pyogenes,* and a strain of *Staphylococcus aureus* which was resistant to the antibiotic methicillin. Data from tests with these organisms is shown in Table 1.

It can be seen from the results of the evaluation that Compounds 1 and 2 were most effective in control of *Staphylococcus aureus* and that Compound 1 is preferred for control of *Streptococcus pyogenes* and *Staphylococcus aureus* 95.

The following examples are intended only to further illustrate the invention and are not intended to limit the scope of the invention which is defined by the claims.

EXAMPLE 1

2,3-Dihydro-5,8-dihydroxy-6-methoxy-2-hydroxymethyl-3-(2-hydroxypropyl)-1,4-naphthalenedione A 1200 L jacketed stainless steel tank was filled with 660 L water in which the following chemicals were dissolved in their respective amounts: $NH_4NO_3$, 264 g; KCl, 198 g; $MgSO_4$, 109 g; $NaH_2PO_4$, 66g; $CaCL_2 \cdot 2H_2O$, 26.4 g; $H_3BO_3$ 3.66 g; $FeSO_4$, 3.30 g; $MnSO_4$, 2.0 g; $ZnSO_4$, 2.71 g; $Na_2MoO_4$, 1,65 g; and $CuSO_4$, 0.25 g. Sucrose, 13.6 kg, was dissolved in 40 L of water, autoclaved at 120° C. for 30 minutes, and added to the tank.

Inoculum for the tank was prepared from V-8 agar slants of *Fusarium solani* NRRL No. 15980 stored at 27° C. in screw-cap culture tubes. Ten ml of sterile distilled water was added to a tube, the tube was shaken vigorously to produce a spore suspension, and one ml of this suspension was added to each of several 500 ml Erlenmeyer flasks containing 200 ml of the above medium. These flasks were incubated for three days at 27° C. on a reciprocal shaker at 150 rpm. Three flasks, containing a total of 600 ml of inoculum, were added to the aforementioned tank. Temperature of the tank was adjusted to 22° C. and maintained at this level for the duration of the fermentation. Aeration was provided with a perforated stainless steel tube in the tank bottom, and was adjusted to provide 5–6 ppm dissolved oxygen initially. Initial pH of the culture was adjusted to 4.86 with 6 N HCl. After 17 hours, growth of the culture had reduced the pH to 2.53.

The fermentation was monitored daily and the pH maintained between 2.53 and 2.71. After four days, aeration was diminished to provide an average dissolved oxygen level of 1.1 ppm. On the seventh day, the culture pH increased to 3.55 as a result of natural fermentative activity. At this point the mycelial density of the culture was 3.1 g/L dry weight. The fermentation was terminated by filtering the culture through cloth bags to remove the fungal mycelium.

Compounds produced in the fermentation were recovered from the filtrate by passing the filtrate through glass columns packed with Amberlite XAD-7 polymeric adsorbent resin. Compounds adsorbed to the resin were eluted with acetone, and the acetone was removed from the column eluate on a vacuum rotary evaporator. The residual water was cooled and filtered, removing 9.5 g of crystals (predominantly cis- and trans-dihydrofusarubin) which were discarded. The filtered water was extracted four times with equal volumes of ethyl acetate, the extracts combined, purged of water with sodium sulfate, filtered, and taken to dryness on a vacuum rotary evaporator. Solids remaining in the evaporator flask were dissolved in chloroform, and chromatographed on a 5×20 cm silica gel column. The column was packed with silica gel type 60 (70–230 mesh ASTM) which had been deactivated with acetic acid and water, rinsed with acetone and then chloroform. Elution of the column was begun with chloroform, followed by chloroform-acetone (98-2), (95-5), and (90-10) to remove less polar compounds. These fractions were discarded. The product was eluted with chloroform-acetone 85-15, and further purified by preparative TLC on 1 mm silica gel HF 60 plates developed in chloroform-methylene chloride-acetic acid-methanol (140-50-4-4). The compound was crystallized from ethyl acetate as light red crystals, m.p. 135° C. Determination of structure was made with MS and with $H^1$ NMR 270 MHz, using TMS as internal standard in deuterated chloroform. The MW was 310.

EXAMPLE 2

2,3-Dihydro-5-hydroxy-4-hydroxymethyl-8-methoxy-2-methyl-naphtho [1,2-b]furan-6,9-dione The compound of Example 1 was chromatographed on a 1 mm preparative TLC plate in the solvent system described in Example 1. The plate was allowed to stand 18 hours at ambient temperatures whereupon the compound of Example 1 was converted almost entirely to the above compound. The compound was purified by TLC and crystallized from methylene chloride-hexane as red crystals, m.p. 202°–203°. Its structure was established with NMR and mass spectral analyses, and was determined to have a molecular weight of 290.

EXAMPLE 3

5,8-Dihydroxy-2-methoxy-6-hydroxymethyl-7-(2-hydroxypropyl)-1,4-naphthalenedione Fifteen mg of the compound produced in Example 2 was suspended in 10 ml of water with 0.8 g of potassium hydroxide. This mixture was heated for 30 min at 70° C. The solution was cooled, extracted with ethyl acetate, and the ethyl acetate extract reduced in volume on a vacuum rotary evaporator. The concentrated product was separated by TLC on silica gel GF plates, developing with chloroform-methylene chloride-methanol-acetic acid (140-50-4-4). The compound was crystallized from ethyl acetate as red crystals, m.p. 206°–212°.

The compound had a molecular weight of 308 and the structure shown in FIG. 1 as determined by mass spectral and NMR analyses.

EXAMPLE 4

Microbiological Assay Procedure

Antimicrobial activity of compounds was determined against a group of bacterial pathogens, using a broth microdilution assay. Pathogens tested included *Staphylococcus aureus, Streptococcus pyogenes, Escherichia coli, Serratia marcescens, Proteus vulgaris, Klebsiella pneumoniae, Salmonella typhi,* and *Pseudomonas aeruginosa.* Activity against plant pathogenic bacteria was tested by applying acetone solutions of compounds to 14 mm Whatman No. 1 filter paper discs, drying and placing four discs/plate on freshly inoculated Kings medium B plates. *Pseudomonas cepacia, P. cichorii, P. fluorescens, P. syringae pv. phaseolicola, P. viridiflava,* and *Xanthomonas campestris* were exposed to discs containing 20 μg of compound; *Curtobacterium flaccumfaciens pv. poinsettiae* (formerly *Corynebacterium poinsettiae*) was tested at 20, 40, and 80 μg/disc. Using a similar assay procedure, *Alternaria citri, Colletotrichum gloeosporioides, Diplodia natalensis, Fusarium solani, F. oxysporum, Geotrichum candidium, Phomopsis citri,* and *Phytophthora parasitica* were tested to determine the antifungal properties of the compounds.

None of the compounds exhibited any antimicrobial activity against any of the gram-negative human and plant pathogenic bacteria, or against any of the fungi tested. They were, however, effective against gram-positive bacteria. Of the three, compound 1 was the most effective, inhibiting growth at 0.5–1 ppm. The only gram-positive plant pathogen tested, *Curtobacterium flaccumfaciens pv. poinsettiae,* was also inhibited by compounds 1–3. When tested at 20, 40, and 80 μg/disc on Kings medium B plates, compound 2 was most active, followed by 1 and 3.

It is understood that the foregoing detailed description is given merely by way of illustration and that modification and variations may be made therein without departing from the spirit and scope of the invention.

TABLE I

| | | Antibacterial activity (MIC)[a] microorganism[b] | | |
|---|---|---|---|---|
| No. | Compound | A | B | C |
| 1. | 2,3-Dihydro-5,8-dihydroxy-6-methoxy-2-hydroxymethyl-3-(2-hydroxypropyl)-1,4-naphthalenedione | 1 | 0.5 | 4 |
| 2. | 2,3-dihydro-5-hydroxy-4-hydroxymethyl-8-methoxy-2-methyl-naphtho[1,2-b] furan-6,9-dione | 4 | 64 | — |
| 3. | 5,8-dihydroxy-2-methoxy-6-hydroxymethyl-7-(2-hydroxypropyl)-1,4-naphthalenedione | 1 | 64 | — |

[a]MIC = minimum concentration of compound (μg/ml) resulting in complete suppression of microbial growth
[b]A = *Staphylococcus aureus*
B = *Streptococcus pyogenes*
C - *Staphylococcus aureus* 95 (resistant to methicillin)

We claim:

1. A method for controlling bacteria comprising applying to the locus of said bacteria an antibiotically effective amount of a substantially pure or formulated naphthoquinone selected from the group consisting of: 2,3-dihydro-5,8-dihydroxy-6-methoxy-2-hydroxymethyl-3-(2-hydroxypropyl)-1,4-naphthalenedione; 2,3-dihydro-5-hydroxy-4-hydroxymethyl-8-methoxy-2-methyl-naphtho[1,2]furan-6,9-dione; and 5,8-dihydroxy-2-methoxy-6-hydroxymethyl-7-(2-hydroxypropyl)-1,4-naphthalenedione.

2. A method as described in claim 1 wherein said naphthoquinone is 2,3-dihydro-5,8-dihydroxy-6-methoxy-2-hydroxymethyl-3-(2-hydroxypropyl)-1,4-naphthalenedione.

3. A method as described in claim 1 wherein said naphthoquinone is 2,3-dihydro-5-hydroxy-4-hydroxymethyl-8-methoxy-2-methyl-naphtho[1,2-]furan-6,9-dione.

4. A method as described in claim 1 wherein said naphthoquinone is 5,8-dihydroxy-2-methoxy-6-hydroxymethyl-7-(2-hydroxypropyl)-1,4-naphthalenedione.

* * * * *